United States Patent [19]

Gilligan et al.

[11] 4,093,623

[45] June 6, 1978

[54] METHOD OF PREPARING THE ACID COPPER SALT OF 5-NITROTETRAZOLE

[75] Inventors: William H. Gilligan, Washington, D.C.; Mortimer J. Kamlet, Silver Spring, Md.

[73] Assignee: The United States of America as represented by the Secretary of the Navy, Washington, D.C.

[21] Appl. No.: 794,197

[22] Filed: May 5, 1977

[51] Int. Cl.² ............................................. C07F 1/08
[52] U.S. Cl. ..................................................... 260/299
[58] Field of Search ......................................... 260/299

[56] References Cited

U.S. PATENT DOCUMENTS

| 2,066,954 | 1/1937 | von Herz | 260/299 |
| 3,965,951 | 6/1976 | Scott et al. | 149/23 |

OTHER PUBLICATIONS

Taylor et al., Symp. Chem. Probl. Connected Stab. Explos. [Proc.], 3rd 1973, (Publ. 1974), pp. 43–46.
Bates et al., Search for New Detonators, paper presented at Proceedings of the International Conference on Research in Primary Explosives, 17,18 & 19, Mar. 1975.

Primary Examiner—Donald G. Daus
Assistant Examiner—Diana G. Rivers
Attorney, Agent, or Firm—R. S. Sciascia; A. L. Branning; R. D. Johnson

[57] ABSTRACT

A process for preparing the acid copper salt of 5-nitrotetrazole by slowly adding an aqueous solution of a strong inorganic acid (e.g., $H_2SO_4$ or $HNO_3$), 5-aminotetrazole, and a small amount of a water soluble cupric salt (e.g., $CuSO_4 \cdot 5H_2O$) to an aqueous solution of a water soluble cupric salt (e.g., $CuSO_4 \cdot 5H_2O$) and sodium nitrite in a 25 to 100 percent stoichiometric excess. The presence of the cupric salt in the initial 5-aminotetrazole, acid solution prevents the occurrence of minor explosions and the large excess of sodium nitrite produces an easily filtered product rather than a gel. The acid copper salt of nitrotetrazole is used in the preparation of mercuric 5-nitrotetrazole which is useful as a primary explosive in detonators.

12 Claims, No Drawings

METHOD OF PREPARING THE ACID COPPER SALT OF 5-NITROTETRAZOLE

BACKGROUND OF THE INVENTION

This invention relates to tetrazoles and more particularly to the metal salts of 5-nitrotetrazole.

Lead azide is one of the most common primary explosives used in detonators. It has been in widespread use for the past 50 years not only in the United States but throughout the world. Despite its almost universal acceptance, its service life is often shortened because of ready hydrolysis in the precence of moisture and carbon dioxide. One of the by-products of hydrolysis is hydrogenazide which in the presence of copper or copper alloys can form various copper azides some of which are even more sensitive, particularly to electrostatic discharge, than lead azide itself. The presence of copper azides is believed to have caused a number of fatal accidents during the handling and storage of munitions, and is also throught to be a factor in premature firings.

Preliminary screening by the British and by the United States Navy indicated that mercuric 5-nitrotetrazole was a promising replacement for lead azide in detonators. Mercuric 5-nitrotetrazole was first reported in 1932 by E. Von Herz in U.S. Pat. No. 2,006,954. He prepared the mercuric 5-nitrotetrazole via the following three step process:

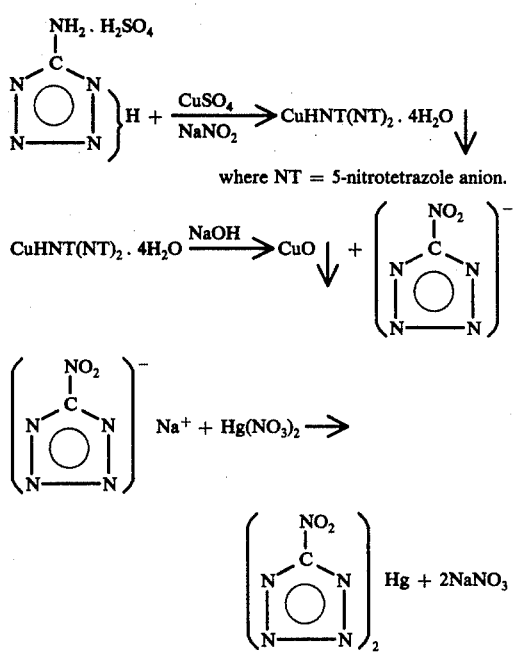

In the first step [I], 5-aminotetrazole was reacted with copper sulfate and sodium nitrite in acid solution to produce the acid copper salt of 5-nitrotetrazole. The Von Herz patent gives the following structure for the acid copper salt of 5-nitrotetrazole

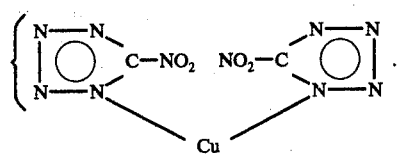

The second step [II] consisted of using sodium hydroxide to convert the acid copper salt of 5-nitrotetrazole into sodium 5-nitrotetrazole. Finally, in the third step [III], sodium 5-nitrotetrazole was reacted with mercuric nitrate to produce mecuric 5-nitrotetrazole.

During initial experimentation with the von Herz procedure by the U.S. Navy, several problems were encountered. First, during the diazotization there was a continuous series of minor detonations, which while not harmful in themselves, were pschologically disturbing and did on occasion break glassware. Moreover, there was the possibility that the potentially dangerous (in the dry state) acid copper 5-nitrotetrazole salt would be spilled over adjacent surfaces as a result of these detonations. Second, upon completion of the diazotization, the acid copper salt was present as a voluminous gel-like precipitate which required long periods (6 hours or longer) to separate by filtration and to wash free of impurities. This would seriously hamper scale-up operations where large quantities would have to be processed.

SUMMARY OF THE INVENTION

Accordingly, one object of this invention is to provide a process for preparing the acid copper salt of 5-nitrotetrazole which is free of minor detonations.

Another object of this invention is to provide a process which will produce a product acid copper salt of 5-nitrotetrazole which can be easily filtered rather than a gel.

A further object of this invention is to substantially reduce the time required to purify the product acid copper salt of 5-nitrotetrazole.

These and other objects of this invention are accomplished in the process of preparing the acid copper salt of 5-nitrotetrazole having the composition

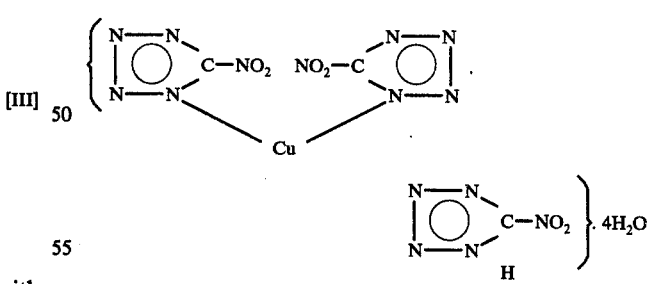

which comprises slowly adding a solution of 5-aminotetrazole and a strong inorganic acid in water to a solution of a water soluble cupric salt and sodium nitrite in water, by (1) adding small amounts of a water soluble cupric salt to the 5-aminotetrazole-acid solution to prevent the build up of detonation sensitive 5-diazotetrazole in the solution while it is being slowly added to the cupric salt-sodium nitrite solution; and (2) using sodium nitrite in an excess of from 25 to 100 percent.

The acid copper salt of 5-nitrotetrazole is a useful intermediate in the preparation of mercuric 5-nitrotetrazole which is useful as a primary explosive in detonators.

DETAILED DESCRIPTION OF THE PREFERRED EMBODIMENT

CAUTION: the acid copper salt, the sodium salt, and the mercuric salt of 5-nitrotetrazole are dangerous explosives which require special handling. Before attempting to prepare any of these compounds please read the notes of caution in the example section.

The present invention involves improvements in the first step of the Von Herz process discussed in the background of the invention. In this first step of the von Herz process, one mole of $CuSO_4.5H_2O$, three moles of 5-aminotetrazole monohydrate, and 6 moles of sodium nitrite are reacted under typical Sandmeyer conditions to form one mole of the copper acid salt of 5-nitrotetrazole

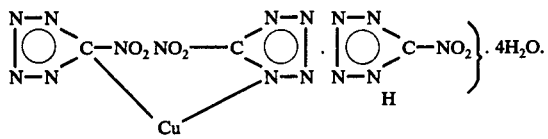

The specific procedure is to form a first solution of 5-aminotetrazole and a strong inorganic acid (e.g., $H_2SO_4$ or $HNO_3$) in water and a second solution of $CuSO_4.5H_2O$ and sodium nitrite in water. The 5-aminotetrazole — acid solution is then added slowly (e.g., dropwise) to the $CUSO_4.5H_2O$ — sodium nitrite solution with stirring and cooling to maintain the reaction temperature in the range of 0° to 30° C.

The first improvement in this step is the addition of a small amount of a water soluble cupric salt to the 5-aminotetrazole-acid solution prior to the addition of that solution to the cupric salt — sodium nitrite solution. This procedure eliminates the minor detonations which normally occur in this first step of the Von Herz process. It appears that these detonations are caused by nitrogen oxide fumes arising from the reaction solution which then react with droplets of 5-aminotetrazole solution on various surfaces of the apparatus to form 5-diazotetrazole. F. R. Benson in "Heterocylic Compounds", 8, p. 1 (1967) points out that 5-diazotetrazole will spontaneously detonate in aqueous solution when the concentration exceeds 1 percent. However, the addition of small amounts of $CuSO_4.5H_2O$ to the 5-aminotetrazole solution prevents any significant build-up of the 5-diazotetrazole by catalyzing its conversion to 5-hydroxyltetrazole:

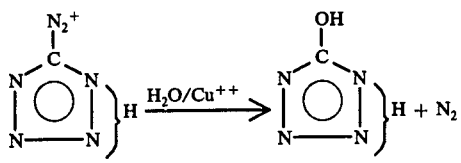

Although $CuSO_4.5H_2O$ was used in the examples, any water soluble cupric salt may be used provided that its anions do not interfere with the formation of the acid copper salt of 5-nitrotetrazole. Because the the cupric ions are a catalyst and not a reactant in the conversion of 5-diazotetrazole into 5-hydroxytetrazole, only small amounts of the cupric salt are required. A molar ratio of cupric ions to 5-aminotetrazole in the range of from 1:100 to 1:25 will work.

The second improvement of this invention comprises the addition of an excess of from about 25 to about 100 percent of sodium nitrite, with an excess of from 50 to 100 percent sodium nitrite being preferred. In theory, two moles of sodium nitrite are required for each mole of 5-aminotetrazole. Any sodium nitrite over this theoretical amount is excess sodium nitrite.

Table 1 presents the compositions of the 5-aminotetrazole-acid solutions and the copper sulfate-sodium nitrite solutions for experiments 1 through 7. Table 2 presents a summary of the results of experiments 1 through 7. Unexpectedly, the time required to wash and filter the product decreases substantially with increasing excess of sodium nitrite.

TABLE 1

| Ex. | #Solution[1] | #2 Solution |
|---|---|---|
| 1 | 51.5 g 5 AT . $H_2$ + 18 cc conc. $H_2SO_4$ in 1500 ml $H_2O$ | 77 g $NaHO_2$ + 75 g Cu $SO_4$ . $5H_2O$ in 750 ml $H_2O$ |
| 2 | 51.5 g 5-AT . $H_2O$ + 18 cc conc $H_2SO_4$ + 2 g Cu $SO_4$ . $5H_2O$ in 1500 ml $H_2O$ | 77 g $NaNO_2$ + 55 g Cu $SO_4$ . $5H_2O$ in 750 ml $H_2O$ |
| 3 | 51.5 g 5-AT . $H_2O$ + 43 ml 70% $HNO_3$ + 2 g Cu $SO_4$ . $5H_2O$ in 1500 ml $H_2O$ | 77 g $NaNO_2$ + 55 g Cu $SO_4$ . $5H_2O$ in 750 ml $H_2O$ |
| 4 | 51.5 g 5-AT . $H_2O$ + 53 ml 70% $HNO_3$+ 2 g Cu $SO_4$ . $5H_2O$ in 1000 ml $H_2O$ | 87 g $NaNO_2$ + 55 g Cu $SO_4$ . $5H_2O$ in 500 ml $H_2O$ |
| 5 | 51.5 g 5-AT . $H_2O$ + 64 ml 70% $HNO_3$+ 2 g Cu $SO_4$ . $5H_4O$ in 1000 ml $H_2O$ | 104 g $NaNO_2$ + 55 g Cu $SO_4$ . $5H_2O$ in 500 ml $H_2O$ |
| 6 | 51.5 g 5-AT . $H_2O$ + 2 g Cu $SO_4$ . $5H_2O$ + 64 ml 70% $HNO_3$ in 600 ml $H_2O$ | 104 g $NaNO_2$ + 55 g Cu $SO_4$ . $5H_2O$ in 300 ml $H_2O$ |
| 7 | 51.5 g 5-AT . $H_2O$ + 28 ml conc $H_2SO_4$ + 2 g Cu $SO_4$ . $5H_2O$ in 700 ml $H_2O$ | 104 g $NaNO_2$ + 55 g Cu $SO_4$ . $5H_2O$ in 300 ml $H_2O$ |

[1]"5-AT . $H_2O$" represents 5-aminotetrazole monohydrate

TABLE 2

| Ex. | %Excess $NaNO_2$ | Washes No. | Washes Vol. | Washes Type[1] | Time for Washes & Filtration | %Yield of Acid Copper Salt of 5-nitrotetrazole |
|---|---|---|---|---|---|---|
| 1 | 16 | 1 | 500 | S | 6 hours | 62% |
|   |    | 2 | 500 | W |         |     |
| 2 | 16 | 1 | 500 | S | 6 hours | 65% |
|   |    | 2 | 500 | W |         |     |
| 3 | 16 | — | —   | — | 2 hours, 25 min. | 63% |
| 4 | 26 | 1 | 400 | N | 45 min. | 74% |
|   |    | 3 | 250 | W |         |     |
| 5 | 57 | 4 | 250 | W | 15 min. | 82% |
| 6 | 57 | 1 | 250 | N | 12 min. | 85% |
|   |    | 3 | 250 | W |         |     |
| 7 | 57 | 1 | 250 | N | 10 min. | — |
|   |    | 3 | 250 | W |         |     |

"S" represents 1.8 N sulfuric acid, "N" represents 1.8 N nitric acid, and "W" represents distilled water.

Examples 1 and 2 duplicate the Von Herz experiment using a 16 percent excess of sodium nitrite. The products were gels which required 6 hours of washing and filtering. Example 3 also used a 16 percent excess of sodium nitrite but took only 2 hours and 45 minutes for washing and filtration; this improvement was apparently due to the use of nitric acid in place of sulfuric acid. In example 4, a 26 percent excess of sodium nitrite reduced the washing and filtration time to 45 minutes. Finally, examples 5, 6, and 7 show that a 56 percent excess of sodium nitrite produces solid products which require 15 minutes or less to wash and filter. Thus, it has unexpectedly been discovered that by increasing the sodium nitrite from an excess of 16 percent to an excess of 56 percent, the time required for collecting and purifying the product is reduced to less than one tenth of the original time. This reduction in time was necessary if the process was to be practical for large scale production.

A method for converting the acid cupric salt of 5-nitrotetrazole into mercuric 5-nitrotetrazole is disclosed in Example 1 of U.S. Pat. No. 2,066,954, entitled "Preparation of Mercuric 5-nitrotetrazole", issued to E. Von Herz on, 1932. Examples 8 and 9 of the present specification also illustrate a method by which the acid copper salt of 5-nitrotetrazole can be converted into the useful mercuric 5-nitrotetrazole.

The general nature of the invention having been set forth, the following examples are presented as specific illustrations thereof. It will be understood that the invention is not limited to these specific examples, but is susceptible to various modifications that will be recognized by one of ordinary skill in the art.

CAUTION: the copper acid salt of 5-nitrotetrazole, $CuHNT(NT)_2$, can be handled safely in the wet state; however in the dry state, it is very sensitive to shock and electrostatic discharge. Air dried sodium 5-nitrotetrazole containing two or more mole-equivalents of water of crystallization is relatively insensitive to shock; it cannot be detonated with a hammer blow. However when completely dry, it is also a sensitive explosive. Both compounds will detonate violently if dropped on a hot plate. All precautions consistent with the handling of potentially dangerous explosive materials should be observed throughout these experiments.

CAUTION: mercuric 5-nitrotetrazole is a powerful primary explosive; it detonates on impact and is also sensitive to friction. All operations should be carried out behind a safety screen with minimum exposure, by experienced personnel.

EXAMPLE 1

(The prior art Von Herz procedure)

A solution of 77 grams of $NaNO_2$ and 75 grams of $CuSO_4.5H_2O$ in 750 ml of water was cooled at 5° C. To this solution was added a solution of 51.5 grams of 5-aminotetrazole monohydrate and 18cc of concentrated sulfuric acid in 1500 ml of water at 40° C at such a rate (dropwise) that the temperature of the reaction mixture was held at 15° C. The reaction mixture was efficiently stirred and cooled throughout this addition. Small explosions were observed during this step. In a similar manner 100 ml of concentrated sulfuric acid were added to the reaction mixture; the mixture was then stirred for an additional 30 minutes. The solution was filtered and the gel-like product was then washed with 500 ml of 1.8N sulfuric acid and then twice with 500 ml batches of distilled water. The filtration and washing require about 6 hours to accomplish. The yield of acid copper salt of 5-nitrotetrazole was 62 percent.

EXAMPLE 2

A solution of 77 grams of $NaNO_2$ and 55 grams of $CuSO_4.5H_2O$ in 750 ml of water was cooled at 5° C. To this solution was added dropwise over a period of about 2 hours a solution of 51.5 grams of 5-aminotetrazole monohydrate, 2 grams of $CuSO_4.5H_2O$, and 18cc of concentrated sulfuric acid in 1500 ml of water. During this addition the reaction mixture was cooled and efficiently stirred; the rate of addition was adjusted to keep the reaction temperature in the range of 8°–10° C. No explosions or minor detonations occurred during the addition. Next a solution of 10 ml of concentrated sulfuric acid in 100 ml of water was added dropwise, with stirring and cooling, to help complete the diazotization reaction. Finally 45 ml of concentrated sulfuric acid in 45 ml of water was added dropwise to the slurry of the copper salt product. The slurry was stirred for 30 minutes and then filtered. The product, the acid copper salt of 5-nitrotetrazole, was a gel. This product was washed first with 500 ml of 1.8N $H_2SO_4$ (25 ml concentrated sulfuric acid in 500 ml of water) and then twice with 500 ml batches of water. The filtration and washes took a total of about 6 hours and the yield of the acid copper salt of 5-nitrotetrazole was 65 percent.

EXAMPLE 3

Example 2 was repeated using 70 percent nitric acid in place of concentrated sulfuric acid. The washing step took about 2 hours and 45 minutes and the yield of the acid copper salt of 5-nitrotetrazole was 63 percent.

EXAMPLE 4

A solution of 87 grams of $NaNO_2$ and 55 grams of $CuSO_4.5H_2O$ in 500 ml of water was cooled at 5° C. To this solution was added dropwise over a period of 1½ hours a solution of 51.5 grams of 5-aminotetrazole monohydrate, 2 grams of $CuSO_4.5H_2O$, and 53 ml of 70 percent nitric acid in 1000 ml of water. During this addition the reaction mixture was cooled and efficiently stirred; the rate of addition was adjusted to keep the reaction temperature in the range of 13° – 15° C. No explosions or minor detonations occurred during this addition. Next a solution of 16 ml of 70 percent nitric acid in 100 ml of water was added dropwise with stirring and cooling. Finally, 69 ml of 70 percent nitric acid in 30 ml of water was added dropwise with stirring and cooling and the mixture was then stirred for an additional 30 minutes. Filtering and washing of the product with 400 ml of 1.8N nitric acid and 3 times with 250 ml batches of water took about 45 minutes. The yield of the acid copper salt of 5-nitrotetrazole was 74 percent.

EXAMPLE 5

Example 4 was repeated with the amount of $NaNO_2$ increased to 104 grams. Filtration and washing of the product acid copper salt of 5-nitrotetrazole four times with 250 ml batches of water took a total of 15 minutes. The yield of product acid copper salt of 5-nitrotetrazole was 82 percent.

EXAMPLE 6

A solution of 104 grams of $NaNO_2$ and 55 grams of $CuSO_4.5H_2O$ in 300 ml of water was cooled at 5° C. To this solution was added dropwise over a period of 1½ hours a solution of 51.5 grams of 5-aminotetrazole monohydrate, 2 grams of $CuSO_4.5H_2O$, and 64 ml of 70 percent $HNO_3$ in 600 ml of water. During this addition the reaction mixture was cooled and efficiently stirred; the rate of addition was adjusted to keep the reaction temperature in the range of 15°–18° C. No explosions or minor detonations occurred during this addition. The reaction mixture was stirred an additional 15 minutes. Next a solution of 70 ml of 70 percent $HNO_3$ in 30 ml of water was added dropwise with cooling and stirring. After this addition was completed, the reaction mixture was stirred an additional 30 minutes. The solid product was filtered and washed first with 250 ml of 1.8N nitric acid and then three times with 250 ml batches of water.

The filtration and washings took a total of about 12 minutes and the yield of the acid copper salt of 5-nitrotetrazole was 85 percent.

EXAMPLE 7

A solution of 104 grams of $NaNO_2$ and 55 grams of $CuSO_4.5H_2O$ in 300 ml of water was cooled at 5° C. To this solution was added dropwise over a period of 1½ hours a solution of 51.5 grams of 5-aminotetrazole monohydrate, 2 grams of $CuSO_4.5H_2O$, and 28 ml of concentrated sulfuric acid in 700 ml of water (at 35° C). During this addition the reaction mixture was cooled and efficiently stirred; the rate of addition was adjusted to keep the reaction temperature in the range of 15°–18° C. No explosions or minor detonations occurred during this addition. Then a solution of 31 ml of concentrated sulfuric acid in 70 ml of water was added to the reaction mixture in a similar fashion. After this addition was completed the reaction mixture was stirred for an additional 30 minutes. The solid product acid copper salt of 5-nitrotetrazole was filtered and washed first with 250 ml of 1.8 N sulfuric acid and then 3 times with 250 ml batches of water. The filtration and washings took a total of about 10 minutes.

EXAMPLE 8 sodium 5-nitrotetrazole dihydrate

The wet cake of the acid copper salt produced in example 6 was transferred to a 1500 ml beaker and the volume was adjusted to 600 ml with water. The pH of the slurry was adjusted to about 9 with 50 percent sodium hydroxide solution to precipitate copper hydroxide. The slurry was then efficiently stirred and heated to 70° C and digested at that temperature for 30 minutes. The precipitate was allowed to partially settle and was then filtered with suction through a packed layer of "Celite". The precipitate was washed twice with 100 ml of water. The pH of the combined filtrate and washes was adjusted to 4 with concentrated nitric acid. The volume of the solution was reduced to about 350 ml using a rotovac at a bath temperature of 60° C. The solution was cooled to 2° C and the sodium 5-nitrotetrazole product was filtered off. The volume of the filtrate was reduced to 200 ml and a second crop of sodium 5-nitrotetrazole was taken. This process was repeated to obtain still more sodium nitrotetrazole. The crops were combined, redissolved in water, and recrystalized a second time. The sodium nitrotetrazole dihydrate product was air dried. Next, the sodium nitrotetrazole dihydrate was dissolved in acetone on a steam bath and filtered to remove inorganic salts. The filtrate was cooled in an ice bath and the sodium 5-nitrotetrazole dihydrate which precipitated was removed by filtration. The 5-nitrotetrazole dihydrate was recrystalized from acetone a second time and then air dried. Yield of sodium 5-nitrotetrazole dihydrate based on the 5-aminotetrazole starting material of example 6 was 45–55 percent.

EXAMPLE 9 mercuric 5-nitrotetrazole

A $Hg(NO_3)_2$ solution was prepared by dissolving 54.0 grams of red mercuric oxide in 200 ml of 35 percent nitric acid. The solution was filtered and the filtrate was diluted to 250 ml with 35 percent nitric acid.

16.7 grams of sodium 5-nitrotetrazole dihydrate was dissolved in 188 ml of water. 12 ml of 70 percent nitric acid was added and a magnetic stirring bar was placed in the solution. In a separate container, 60 ml of the $Hg(NO_3)_2$ solution was added to 140 ml of water. Both the sodium 5-nitrotetrazole solution and the $Hg(NO_3)_2$ solution were heated to 75° C in a water bath. Both of the solutions were removed from the bath and the $Hg(NO_3)_2$ solution was quickly added to the sodium 5-nitrotetrazole solution. The mixture was allowed to cool gradually to 30° C with continous stirring at the slowest possible speed while the mercuric 5-nitrotetrazole salt crystallized. The stirring was then stopped to allow the mercuric salt to settle and the supernatant liquid was decanted off. The solids were transferred to a "Nalgene" beaker by means of a water wash bottle. 200 ml of water was added, the mixture was swirled, the mercuric 5-nitrotetrazole allowed to settle and the water was decanted off. About ⅓ of the solid product was transferred to a small "Nalgene" buchner funnel (#2 Whatman paper) by means of a water wash bottle and then was washed consecutively with 50 ml of water, twice with 50 ml of methanol, and finally with 50 ml of methylene chloride. The solid product was then air dried on the funnel. The dried mercuric 5-nitrotetrazole salt was then carefully transferred to a weighed widemouth conductive plastic container by gently pouring the contents (mercuric salt) of the funnel into the plastic container. After it was weighed, the mercuric 5-nitrotetrazole salt was placed into a blast-proof container. This procedure was repeated for the remainder of the product. Yield of mercuric 5-nitrotetrazole was 75 to 80 percent based on sodium 5-nitrotetrazole.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. In the Von Herz process of preparing the acid copper salt of 5-nitrotetrazole having the composition which comprises slowly adding a solution of 5-aminotetrazole and a strong inorganic acid in water to a solution of a compatible water soluble copper (II) salt and sodium nitrite in water in accordance with the method of Sandmeyer, the improvement comprising: using a 25 to 100 percent excess of $NaNO_2$.

2. In the process of claim 1 the improvement comprising using a 50 to 100 percent excess of $NaNO_2$.

3. In the Von Herz process of preparing the acid copper salt of 5-nitrotetrazole having the composition

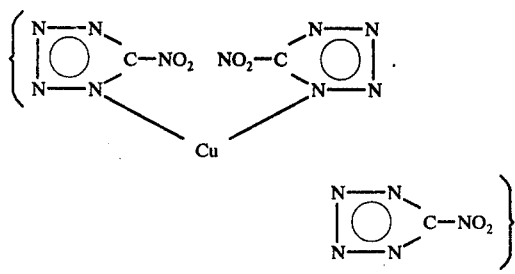

by slowly adding a solution of 5-aminotetrazole and a strong inorganic acid in water to a solution of a compatible water soluble copper (II) salt and sodium nitrite in water in accordance with the method of Sandmeyer, the improvement comprising:

adding small amounts of the water soluble copper (II) salt to the 5-aminotetrazole-acid solution to prevent the build up of detonation sensitive 5-diazotetrazole in the 5-aminotetrazole-acid solution during the addition of the 5-aminotetrazole-acid solution to the copper (II) salt-sodium nitrite solution.

4. The process of claim 1 wherein the strong inorganic acid is sulfuric acid.

5. The process of claim 1 wherein the strong inorganic acid is nitric acid.

6. The process of claim 1 wherein the compatible water soluble copper (II) salt is $CuSO_4 \cdot 5H_2O$.

7. The process of claim 2 wherein the strong inorganic acid is sulfuric acid.

8. The process of claim 2 wherein the strong inorganic acid is nitric acid.

9. The process of claim 2 wherein the compatible water soluble copper (II) salt is $CuSO_4 \cdot 5H_2O$.

10. The process of claim 3 wherein the strong inorganic acid is sulfuric acid.

11. The process of claim 3 wherein the strong inorganic acid is nitric acid.

12. The process of claim 3 wherein the compatible water soluble copper (II) salt is $CuSO_4 \cdot 5H_2O$.

* * * * *